(12) United States Patent
Kuroda et al.

(10) Patent No.: US 6,719,488 B2
(45) Date of Patent: Apr. 13, 2004

(54) SOIL PF VALUE MEASURING METHOD, AND IRRIGATION CONTROL METHOD AND IRRIGATION CONTROL DEVICE

(75) Inventors: Tetsuo Kuroda, Kanagawa (JP); Hidemitsu Otsuka, Tokyo (JP); Ichiro Kamiya, Tokyo (JP); Yuzo Narasaki, Kanagawa (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 10/149,432

(22) PCT Filed: Dec. 21, 2000

(86) PCT No.: PCT/JP00/09090
§ 371 (c)(1),
(2), (4) Date: Jun. 24, 2002

(87) PCT Pub. No.: WO01/46681
PCT Pub. Date: Jun. 28, 2001

(65) Prior Publication Data
US 2003/0024155 A1 Feb. 6, 2003

(30) Foreign Application Priority Data
Dec. 22, 1999 (JP) ............................................. 11-364693

(51) Int. Cl.$^7$ .............................................. G01R 27/26
(52) U.S. Cl. .............................. 405/36; 73/73; 324/690
(58) Field of Search ......................... 405/36, 37; 73/73; 324/686, 690

(56) References Cited

U.S. PATENT DOCUMENTS 5,898,310 A * 4/1999 Liu ............................. 324/690

FOREIGN PATENT DOCUMENTS

| JP | 1-317342 | 12/1989 |
| JP | 7-244040 | 9/1995 |
| JP | 9-271276 | 10/1997 |
| JP | 10-078401 | 3/1998 |
| WO | 97-09590 | 3/1997 |

OTHER PUBLICATIONS

American Geophysical Union, Water Resources Research, vol. 16, Jun. 1980, Nov. 3, pp. 574–582.
Saishin Dojogaku, Modern Soil Science, 1977, pp. 101–107 (w/partial English Translation).
Dojo Kankyo Burnsekiho, Analysis of Soil Environement, 1997, pp. 48–65 (w/partial English Translation).
Tsuchi no Kankyoken, Environment of Soil, 1997, pp. 30–32, 72–76.
Dojo Shindan no Hoho to Katsuyo, Soil Analysis—Methods and Aplications, 1996, pp. 72–77.
Makoto Nakajima et al, Proceedings of 1997 Spring Meeting of Japanese Association of Groundwater Hydrology, 1997, pp. 18–23.
Haruhiko Horino and Toshisuke Maruyama, TDR Measurment of Soil Moisture with Three–Line Probe, Collected Papers of Japanese Society of Irrigation, Drainage and Reclamation Engineering, 1993, pp. 168, 119–120.
Kitahei Tatsumi et al, Field Measurement of Soil Moisture By FDR, Collected Papers of Japanese Society of Irrigation, Drainage and Reclamation Engineering, 1996, No. 182, pp. 31–38.

* cited by examiner

*Primary Examiner*—Robert E. Pezzuto
*Assistant Examiner*—Tara L. Mayo
(74) *Attorney, Agent, or Firm*—Oblon, Spivak, McClelland, Maier & Neustadt, P.C.

(57) ABSTRACT

A method and an apparatus for measuring the moisture content of the soil in order to enable pF value based control of irrigation in cultivation on the soil, as well as a method and an apparatus which use the first-mentioned method and apparatus to enable pF value based control of irrigation. To attain these objects, the invention provides a method for measuring the pF value (soil moisture tension) of the soil, comprising the steps of (a) preliminarily determining the correlation between pF value and volumetric water content of the soil to be measured, (b) measuring the volumetric water content of the soil, and (c) converting the value of the volumetric soil water content of the soil measured in the above step (b) to the corresponding pF value on the basis of the correlation between pF value and volumetric water content predetermined in the above step (a). Also a method and an apparatus for controlling the irrigation of the soil based on the measurement of the pF value by the method.

16 Claims, 6 Drawing Sheets

Fig.5
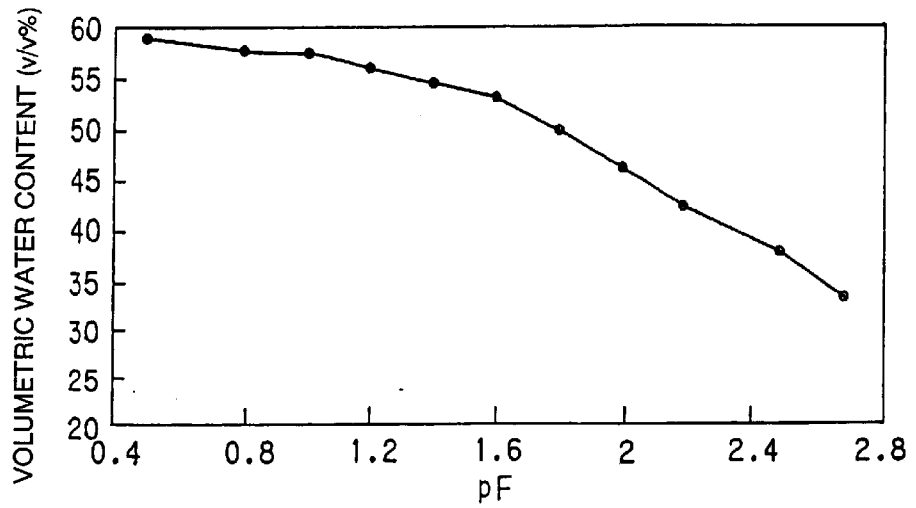
(a) FINE PARTICULATE SAMPLE
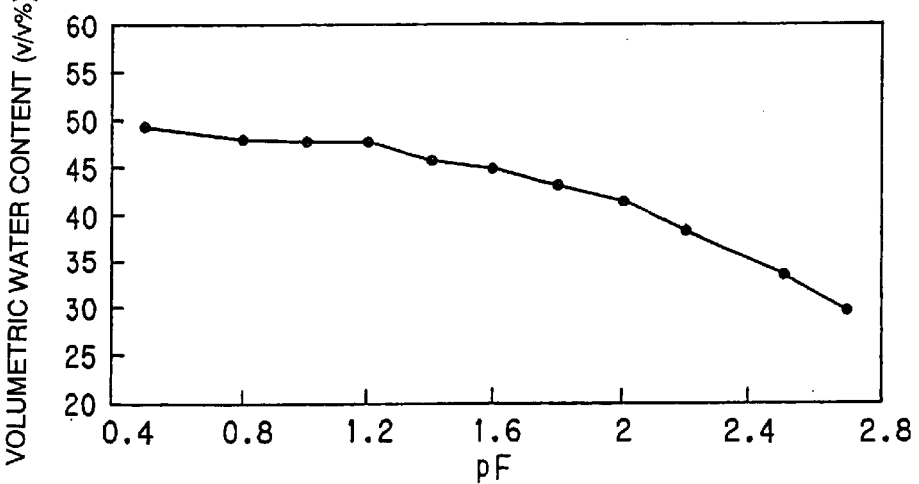
(b) MIXED SAMPLE
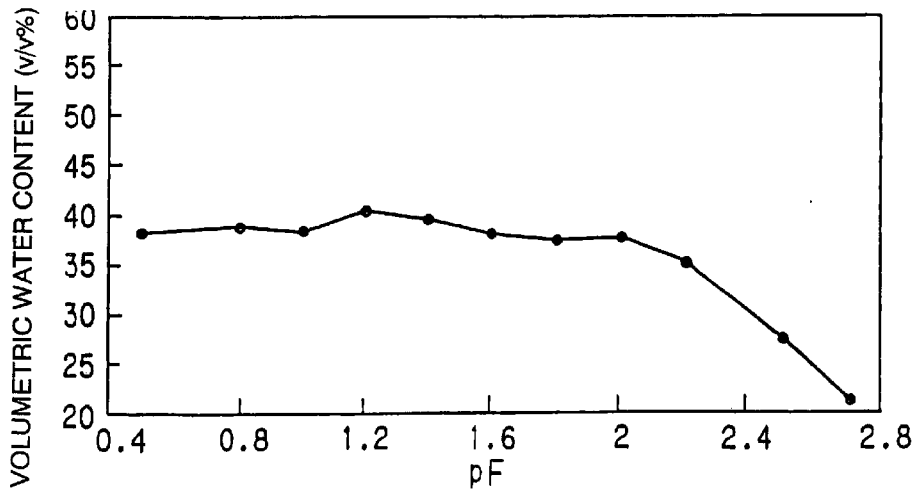
(c) PUMICE SAMPLE

SOIL PF VALUE MEASURING METHOD, AND IRRIGATION CONTROL METHOD AND IRRIGATION CONTROL DEVICE

TECHNICAL FIELD

This invention relates to the technology of measuring the water content of the soil, as well as a method of cultivation and an apparatus for cultivation that use the technology. The invention relates particularly to a method that measures the water content of the soil and performs pF conversion to determine its pF value in order to facilitate soil management and enable the saving of water, resources and labor, as well as a method and an apparatus for irrigation control which control the supply of water or nutrient (nutrient solution) to the soil on the basis of the measured pF value. The term "soil" as used herein refers to all materials that support the underground parts of plants such as root and subterranean stem; the term includes not only what is commonly called "soil" but also solid mediums such as sand particles, gravel stones, smoked coal and pumice.

BACKGROUND ART

In their cultivation on the soil, the growth of field crops is largely dependent on the soil-moisture content which can be controlled in various ways; in lands of high moisture content, enhanced drainage is performed whereas in lands of low moisture content, irrigation is performed, which is enhanced in dry seasons. In order to ensure a favorable growth of field crops, the accurate moisture content in the soil must be known.

High-grade vegetables such as corn salad and tomato are usually grown in crop fields but sometimes they need to be cultivated in open-area facilities and greenhouses with the environment being precisely controlled as in industrial plants. This cultivation method is called "protected cultivation". Cultivation in crop fields involves supplying fertilizers and other nutrient sources to the soil while applying water to the crop. In protected cultivation, solution culture is preferably adopted, according to which sand particles, gravel stones, smoked coal, etc. are laid down to make mediums which are supplied with aqueous nutrient solutions by irrigation. However, optimum irrigation has not always been achieved in the actual cultivation, particularly in solution culture.

Solution culture can be classified into three types, hydroponics, aeroponic and solid-medium culture. In solid-medium culture, continuous drip irrigation is commonly adopted. In continuous drip irrigation, timer or otherwise controlled automatic irrigation is the dominant approach but optimum irrigation is not always assured. This is because the amount in which the nutrient solution is absorbed by crops being cultured is dependent on various factors including the amount of solar radiation, as well as the temperature and humidity in the greenhouse. For example, the transpiration from crops being cultivated is very high if the amount of solar radiation is large and the greenhouse has high temperature and low humidity. On the other hand, the transpiration from crops being cultivated decreases on a rainy day. The absorption of nutrients by crops being cultivated is also largely dependent on the process of their growth and if they have grown up, the absorption of nutrients becomes very high. It is known that high-quality fruits with high sugar content can be obtained by reducing the water supply after they have grown to a certain extent. However, timer and otherwise controlled automatic irrigation is incapable of meeting those environmental conditions for cultivated crops at various stages of their growth unless the number of irrigations, the start time of irrigation and the duration of irrigation are daily set for new values.

This is not "timer or otherwise controlled automatic irrigation" in the true sense of the term and it is highly doubtful whether optimum irrigation can really be achieved. For these reasons, timer or otherwise controlled automatic irrigation often involves over-irrigation in order to prevent wilting or other troubles of crops but then it has been impossible to avoid root rot due to over-irrigation and increased drainage (i.e., increased quantities of nutrient solution and water are discarded).

Speaking of the relationship between the moisture content of the soil and field crops, not all of the water in the soil is available to field crops and bound water in the soil is not available to the growth of field crops. The moisture content of the soil also varies with weather changes; the soil is filled with water if there is a heavy rain but thereafter the water is gradually absorbed by the lower soil layers and the moisture content of the soil decreases. The soil filled with water is equivalent to what occurs in hydroponics and its air permeability is too low to be suitable for open-field cultivation. If, at the subsequent stage, the moisture content of the soil decreases considerably to a level below a certain threshold, the root is no longer capable of sucking up water and the capillary network in the root is interrupted, causing the root to wither. Once this stage has been reached, the root will no longer recover from withering even if it is supplied with water; therefore it is necessary that the moisture content of the soil be kept higher than the lower limit defined by that stage.

Since the wetness of the soil is determined by the potential of water in the soil, it is held inappropriate that the wetness of the soil which is related to the cultivation of field crops should be simply expressed by the moisture content of the soil. A more preferred method is by expressing the wetness of the soil on the basis of its water potential.

One of the factors that describe the wetness of the soil is the "pF value". Being first proposed by R. K. Schofield in 1935, the pF value is an index for the matrix potential as a soil-water potential. The matrix potential is a drop in chemical potential resulting from the interactions between water and soil particles, as exemplified by capillary, intermolecular and Coulomb forces. Stated briefly, the matrix potential is the force by which water molecules are attracted to soil particles. The common logarithm of the absolute value of a matrix potential expressed by a graduation on a water column (cm) is called the pF value. The soil-water potential $\phi$ expressed by a graduation on a water column (cm) and the pF value are related by $pF=\log(-10.2\ \phi)$.

The pF value is a quantity that describes the quality of water in the soil (which is a nutrient in solution culture). A near-zero pF value represents the state of the soil that is filled with water. The moisture that remains in the soil 24 hours after rainfall or irrigation is called field capacity and has a pF value of about 1.7; the water which is present in the range from the field capacity to the primary wiltig point (pF of 3.8) at which a crop starts to wither is called "available water". In practice, however, the growth of crops begins to experience troubles at a point where more water exists than at the primary wiltig point. The point is where the capillary network in a crop's root is interrupted to stop the movement of water from the root. Called the rupture of capillary network, this point has a pF of about 2.7. Hence, for cultivation of crops, it is generally held that the pF value is suitably within the range from 1.7 to 2.7. For these reasons, the moisture present in the pF range of 1.7–2.7 is called "easily available water" and for cultivation of field crops in the soil, it is required to maintain this easily available water in the pF range of 1.7–2.7. The descriptions of the pF value and the soil-water potential may be found in "Dojo Kankyo Bunsekiho (Analyses of Soil Environment)", ed. by the Editors' Committee on Analyses of Soil Environment under the supervision of the Society of Soil and Fertilizers of Japan, published by Hakuyusha, first printing in 1997, pp. 48–51; "Tsuchi no Kankyoken (Environment of Soil)", ed. under the supervision of Shingo Iwata, published by Fuji-Techno System, 1997, pp. 72–76; "Dojo Shindan no Hoho to Katsuyo (Soil Analysis—Methods and Applications)", Shunrokuro Fujiwara et al., published by Nosangyoson Bunka Kyokai, Corporation, 1996, pp. 72–77; and "Saishin Dojogaku (Modern Soil Sicence)", ed. by Kazutake Kyuma, published by Asakura Shoten, 1997, pp. 101–107.

In the cultivation of field crops in the soil, irrigation and other operations are desirably performed on the basis of the pF value.

Among various methods for pF value measurement, tensiometry is known to be capable of direct field measurement on the soil.

A method of measurement that can be effectively used for controlling irrigation in actual cultivation must be capable of direct measurement of how much water can be held by the soil in a particular field. In ordinary fields, therefore, tensiometry is used as a simple method for measuring the pF value of the soil in the interest of management for optimum irrigation and the like. Tensiometry involves the use of an instrument called the tensiometer which consists of a porous ceramic cup (probe) and a rigid transparent poly(vinyl chloride) tube; the tensiometer is buried in the soil and filled with water so that the soil moisture has hydraulic continuity to the water inside the tube through the pores in the probe walls, whereupon the matrix potential of the soil equilibrates with the pressure inside the tube, making it possible to read the pressure inside the tube as the matrix potential of the soil. For details of tensiometry, see, for example, "Dojo Kankyo Bunsekiho", supra, pp. 59–62.

However, the conventional method of tensiometry requires in situ system of replenishment with water and management of the sensor (tensiometer) is quite cumbersome; it is therefore desired to ensure that the pF value of the soil can be measured by a simpler means or with a simpler system. Another difficulty is that depending on the quality of the soil to be measured, the use of tensiometry is sometimes unsuitable.

To be specific, tensiometry cannot be used with soil composed of coarse particles, for example, solid mediums made of coarse particles having porous surfaces such as pumice particles typically used in solution culture.

This is because the particles in the coarse medium do not make intimate contact with the entire surface of the probe and, hence, the water on such particles fail to have intimate contact with the probe surface, making it impossible to achieve correct measurement. Although it has been recognized that irrigation control on the basis of pF value as an index is also desirable in cultivation on solid mediums made of coarse particles, this need has never been met.

Currently, there is no alternative to tensiometry as a method capable of direct pF value measurement in the soil.

One of the methods that are drawing increasing attention today as means for investigating the water retentivity of the soil is by determining the volumetric soil water content from the measurement of its dielectric constant. Two practical approaches toward this goal are TDR (time-domain reflectometry) which determines the dielectric constant of the soil from the propagation time of electric pulses and FDR (frequency-domain reflectometry) which determines the dielectric constant of the soil from the frequency domain characteristics of electric pulses. In addition, ADR (amplitude-domain reflectometry) based on impedance measurement has been proposed as a more convenient and less costly method for measuring the volumetric soil water content. Details of these methods may be found in "Dojo Kankyo Bunsekiho", supra, pp. 62–64; Topp, G. C. et al. (1980), Electromagnetic determination of soil water content: Measurements in coaxial transmission lines, Water Resources Research, 16, 574–582; Haruhiko Horino and Toshisuke Maruyama (1993), TDR Measurement of Soil Moisture with Three-line Probe, Collected Papers of Japanese Society of Irrigation, Drainage and Reclamation Engineering, 168, 119–120; Kitahei Tatsumi et al. (1966), Field Measurement of Soil Moisture by FDR, Collected Papers of Japanese Society of Irrigation, Drainage and Reclamation Engineering, 182, 31–38; Makoto Nakajima et al. (1997), Soil Moisture Measurement by ADR, Proceedings of 1997 Spring Meeting of Japanese Association of Groundwater Hydrology, pp. 18–23. In particular, ADR permits very convenient measurements, assures high degree of correlation, can be performed with a simple and easy-to-maintain instrument for measurement, involves easy handling, and enables continuous measurement in a so-called "maintenance-free" manner. However, the methods mentioned above are intended to determine the volumetric soil water content and are incapable of direct measurement of its pF value.

An object, therefore, of the present invention is to provide means for measuring the pF value of the soil by investigating its water retentivity without using tensiometry.

Another object of the invention is to provide a method in which the pF value of the soil is measured instantaneously and continuously through investigation of its water retentivity and the measured pF value is used to control irrigation. Still another object of the invention is to provide an apparatus for implementing the method.

Yet another object of the invention is to provide a method which provides means capable of measuring, particularly in a continuous manner, the pF value of the soil even if it cannot be measured directly by tensiometry or other methods and which controls irrigation on the basis of the measured pF value. A further object of the invention is to provide an apparatus for implementing this method.

A still further object of the invention is to provide a method for measurement of soil-water content which enables pF value based control of irrigation by using a simple and easy method for measuring the water retentivity of the soil which precludes the use of a tensiometer in solution culture on solid mediums, particularly in the case of porous, large-diameter particles such as pumice particles. Yet another object of the invention is to provide an apparatus for implementing this method. A further object of the invention is to provide a method which enables pF value based control of irrigation in cultivation on solid mediums. A still further object of the invention is to provide an apparatus for implementing the method.

DISCLOSURE OF THE INVENTION

The present inventors conducted intensive studies in order to attain the stated objects and noted that a correlation depending upon the type of the soil, namely, the soil texture, existed between the pF value and the volumetric soil water content that can be measured fairly easily by ADR and other conventional methods described above. It was found that by measuring the volumetric soil water content of interest after determining the correlation between volumetric water content and pF value for that soil, the pF value of the soil could be determined and used to control irrigation. The present invention has been accomplished on the basis of this finding.

Thus, the present invention provides a method for measuring the pF value (soil moisture tension) of the soil, comprising the steps of:

(a) preliminarily determining the correlation between pF value and volumetric water content of the soil to be measured;

(b) measuring the volumetric soil water content; and (c) converting the value of the volumetric soil water content measured in the above step (b) to the corresponding pF value on the basis of the correlation between pF value and volumetric soil water content predetermined in the above step (a).

BRIEF DESCRIPTION OF THE DRAWINGS

FIGS. 5a, 5b and 5c are graphs showing the relationship between volumetric water content and pF value for three mediums, a powder sample (FIG. 5a), a mixed sample (FIG. 5b) and a pumice sample (FIG. 5c)

BEST MODE FOR CARRYING OUT THE INVENTION

Figure 1:
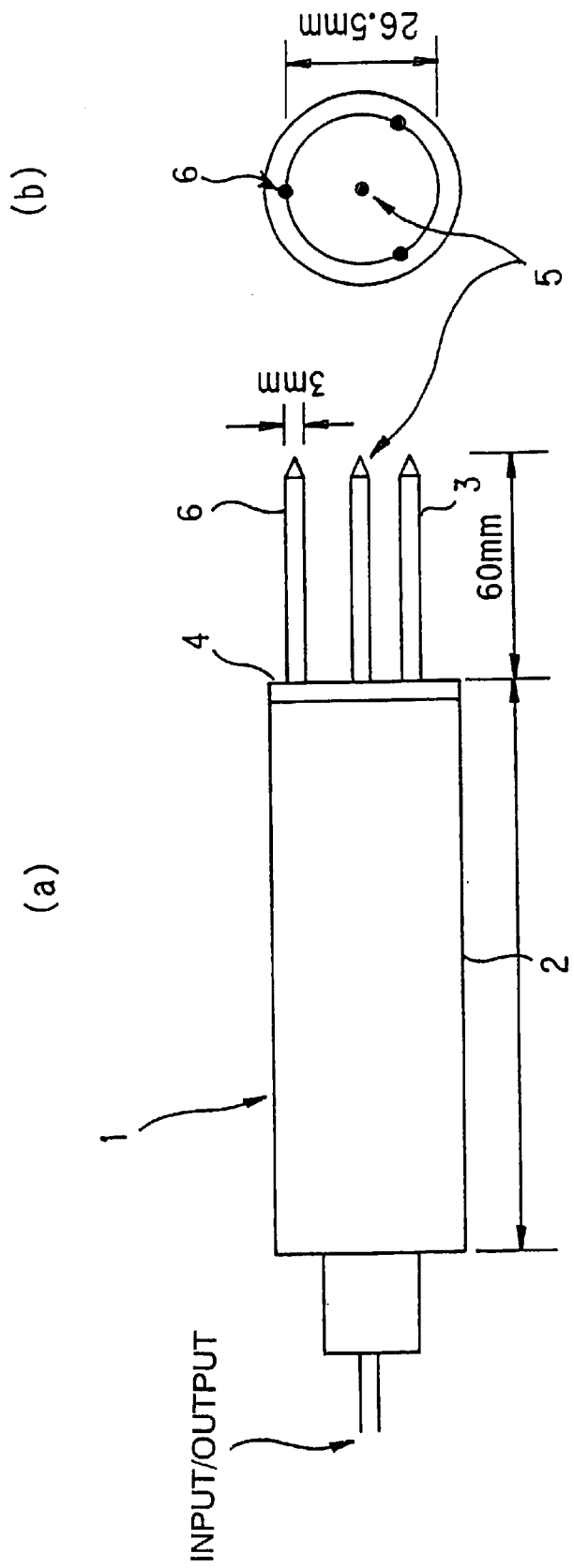
FIG. 1a is a front view showing diagrammatically an instrument for measurement by ADR.
FIG. 1b is a plan view of the instrument.

The methods of the invention are based on the idea of first measuring the volumetric soil water content and then determining its pF value from the measured volumetric soil water content.

The water retentivity of the soil can be expressed by a variety of factors including the volumetric water content and the pF value. One method to measure the volumetric soil water content is gravimetry which involves collecting a sample of the soil to be measured and measuring the weight of the moisture in it. However, this method involving the measurement of a collected soil sample is not applicable in direct in situ measurement of the volumetric soil water content primarily because it does not permit continuous measurement.

A method drawing increasing attention today as means for direct in situ measurement of the volumetric soil water content in a field is the electric pulse approach for measuring the dielectric constant of the soil. Measuring a certain area of the soil, this method experiences small enough variations in measured values and allows for simple and hence desired operations of measurement. In addition, very rapid measurement is possible, continuous measurement is easy to perform and high correlation is provided between the electrical output signal and the volumetric water content. However, the electric pulse approach can measure only the volumetric soil water content and no single means has been developed that relies upon this approach to determine the pF value which is an index for the moisture that is available to plants.

A typical method that relies upon the electric pulse approach is TDR. According to the principle of measurement by TDR, water has a relative dielectric constant of 81 which is by far greater than the values for soil solids (ca. 4) and air (1) and the empirical correlation established between the apparent relative dielectric constant of the soil and its water content is utilized to measure the volumetric soil water content. Specific means of measurement comprises inserting two or three parallel electrodes into the soil, applying microwaves to the electrodes and measuring the propagation time of the interfering reflected wave. If the length of each electrode is written as L and the propagation time of the reflected wave as t, the propagation velocity V of microwaves is given by V=2 L/t. Theoretically, the relative dielectric constant Ka is in inverse proportion to the square of the propagation velocity V of microwaves, so the relative dielectric constant can be determined by $Ka=(C/V)^2$ where C is the speed of light in vacuum.

In a similar method called FDR, the dielectric constant of the soil is determined from the frequency domain characteristics of interfering reflected waves. Both TDR and FDR which can measure the volumetric soil water content are suitable for use in the method of the invention.

On the other hand, these methods have the disadvantage of requiring a costly oscilloscope for measuring the propagation speed of pulses.

ADR has recently been developed as a method that has comparable performance to TDR and FDR and which still allows for simpler measurement. This method is capable of simple and inexpensive measurement of the volumetric water conent through simple impedance measurement. Hence, ADR is more preferred for use in the present invention.

ADR is similar to TDR and FDR in that the principle that the relative dielectric constant Ka of the soil is largely dependent on its volumetric water content (θ) is used to determine θ from the relation Ka–θ. However, ADR differs from TDR and FDR in that the relative dielectric constant Ka is determined by measuring the impedance (Z) of a transmission line over which radio-frequency electric pulses make a round trip via a probe in the soil.

FIGS. 1a and 1b show diagrammatically an ADR operated, soil moisture sensor 1 in a front view (a) and a plan view (b), respectively. The sensor probe consists of a main body 2 and a sensor portion 3; the main body 2 contains a 100 MHz sinusoidal oscillator, a coaxial transmission line section and a measuring electronic circuit, and the sensor portion 3 consists of four parallel stainless steel rods. As shown in FIG. 1b, the center rod of the sensor portion 3 is a signal rod 5 around which three shield rods 6 are arranged to form an electric shield. The sensor portion acts as an additional section to the transmission line and has a value of Z which is substantially dependent on the dielectric constant of the soil within a circle 26.5 mm across that is surrounded by the shield rods 6.

The signal from the oscillator propagates over the transmission line through the sensor probe and if Z of the sensor portion 3 differs from Z of the coaxial transmission line in the main body, a certain amount of signal is reflected back from the junction 4 between the signal rod and the transmission line. The relative proportion of the reflected signal is called the reflection coefficient ρ.

The reflection coefficient undergoes interference by the amplitude of the incident signal which is a cause of the voltage standing wave produced by the interference between the incident wave and the reflected wave, namely, the amplitude of the voltage measured over the length of the transmission line.

Since the initial peak voltage $v_o$ of the transmission line is designed to satisfy a certain relationship with the peak voltage $v_j$ at the junction, the amplitude difference is represented by a relation as functions of the impedance of the transmission line and the impedance of the probe in the soil matrix.

By measuring this amplitude difference, the relative impedance Z of the sensor portion is evaluated and the dielectric constant K is determined by the following formula:

$$Z = \frac{60}{\sqrt{Ka}} \left( F \cdot \frac{r_2}{r_1} \right)$$

where $r_1$ and $r_2$ are the radii of the signal electrode and the shield electrode, and F is the shape factor. From the determined relative dielectric constant Ka of the soil, its volumetric water content θ ($m^3 \cdot m^{-3}$) can be determined by the empirical formula:

$$\theta = -5.3 \times 10^{-2} + 2.92 \times 10^{-2} Ka - 5.5 \times 10^{-4} Ka^2 + 4.3 \times 10^{-6} Ka^3$$

The amplitude of the voltage standing wave has such characteristics that it decreases with increasing soil moisture (increasing relative dielectric constant). Hence, the moisture content of the soil of interest is measured in a separate step by gravimetry or a like method and ADR or some other method is performed to yield an output signal value (e.g. output voltage); by performing repeated measurements at varying moisture contents of the soil, one can obtain a calibrated characteristic curve representing the relationship between the output voltage and the volumetric water content estimated from the soil moisture content and, as a result, one obtains means for providing the correct volumetric soil water content through ADR measurement in the field.

Figure 2:
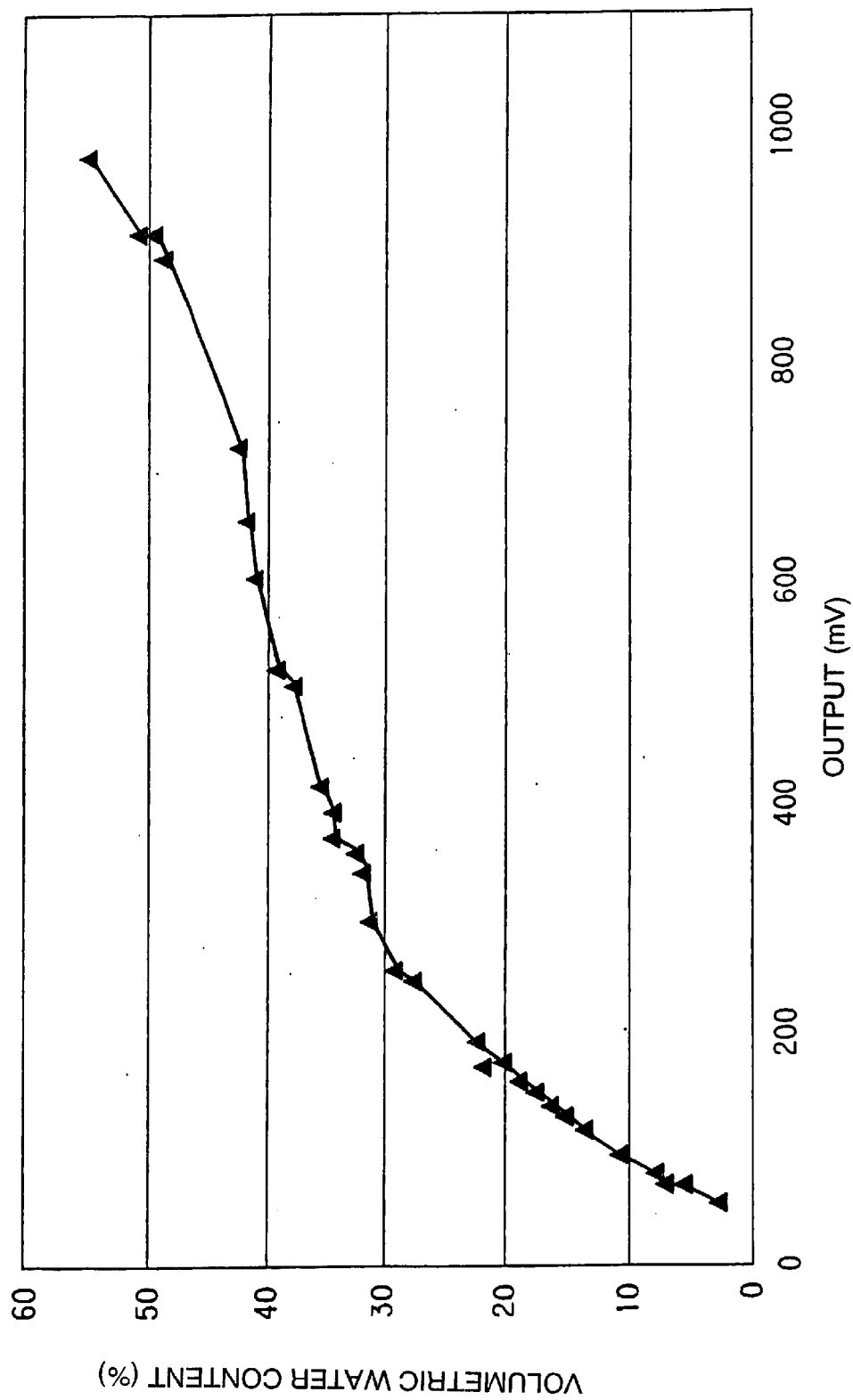
FIG. 2 is a graph showing the relationship between the output voltage of a sensor used in the measurement of the soil of SHIRASU pumice particles by ADR in Example 1 and its volumetric water content θ.

In this way, one can determine the volumetric soil water content by ADR and other methods based on dielectric constant. The relationship between the sensor output voltage in ADR and the volumetric water content θ is shown in FIG. 2, from which one can clearly see the correlation between the two parameters.

As described above, the dielectric constant based methods, especially ADR, enable the volumetric soil water content to be determined in a simple and easy way; ADR which is based on the measurement of average dielectric constant for the soil in a cylindrical portion of a specified diameter has a particular advantage in that the sensor probe need not be in intimate contact with the soil particles and that the volumetric water content can be measured even for soil which is composed of coarse particles such as pumice particles. The foregoing and following descriptions are directed to the method of determining the volumetric water content on the basis of a voltage output from an ADR instrument. It should, however, be noted that in the method of the invention, the volumetric water content may be determined on the basis of other output signal values from the ADR instrument or it may be determined on the basis of output signal values from other sensor types such as a TDR and an FDR instrument.

However, the volumetric soil water content obtained by these measurements, namely, the soil moisture content includes bound water in the soil and other quantities of water not available to plants, so it differs from the pF value which is in good correspondence to the quantity of water that is available to plants.

In the present invention, the result of measurement of the volumetric soil water content typically obtained by ADR is converted to the pF value of the soil.

The matrix potential (pF value) of a soil sample and its volumetric water content are correlated by a characteristic curve depending on the texture of the soil and this curve is called a "moisture retention curve". Known methods for measuring the moisture retention curve of a soil sample, namely, the correlation between its matrix potential and the volumetric water content, include the sand-column method, the suction method, the pressure-plate method and the pressure-membrane method. In all of these methods except the sand-column method, a specified pressure is applied to a soil sample and the weight of the soil at equilibrium is measured to determine the volumetric water content corresponding to the matrix potential; this procedure is repeated at various pressures to construct a moisture retention curve for the soil sample of interest. In the sand-column method, no pressure is applied to the soil sample but a specified position potential is applied by placing it on a sand column and a similar procedure of measurement is followed.

As described above, the existence of a soil texture dependent correlation between the volumetric soil water content and its pF value is noted in the invention and after a moisture retention curve (correlation line) for the soil under analysis is preliminarily determined, the volumetric soil water content is determined by a suitable method such as ADR and the pF value of the soil is determined from the correlation line. The correlation line may be replaced by a conversion table or, if possible, by a mathematical approximation. A preferred means for determining the pF value of the soil from its volumetric water content by means of the correlation line is the use of a processor such as a microcomputer that is loaded with the predetermined correlation line plus a program for receiving an output signal from the ADR instrument and outputting a signal corresponding to the pF value of the soil.

Described on the following pages is the characteristic technique of the invention which comprises the steps of constructing a characteristic line on the basis of an investigated correlation between the volumetric soil water content and its pF value, determining the volumetric soil water content on the basis of dielectric constant and determining the pF value of the soil from the determined volumetric water content on the basis of the preliminarily constructed characteristic line.

In the first step, pF values of the soil that correspond to various volume fractions of water in it and which provide basic data for the construction of a characteristic line correlating the volumetric water content and the pF value (i.e. a moisture retention curve) are determined by a method known in the art. Since the measurement of pF values requires great accuracy, an indoor method is employed. Known indoor methods for the measurement of pF values include the sand-column method, the pressure-plate method, the suction method, the pressure-membrane method and the vapor-pressure method. The sand column method is said to be suitable for the measurement at pF values in the range of 0.5–1.4 and the pressure-plate method at pF values in the range of 1.6–2.7. A method called the "centrifugation method" has been proposed for the measurement of pF values but this has not yet matured to a fully commercial stage. Therefore, one may well say that the pressure-plate method is the most suitable for the purpose of the invention, keeping the soil moisture content within the pF range of 1.7–2.7 where "easily available water" is found. However, other methods including the sand-column method can also be used in the invention.

The pF values of the soil are typically measured by the pressure-plate method as follows.

Figure 3:
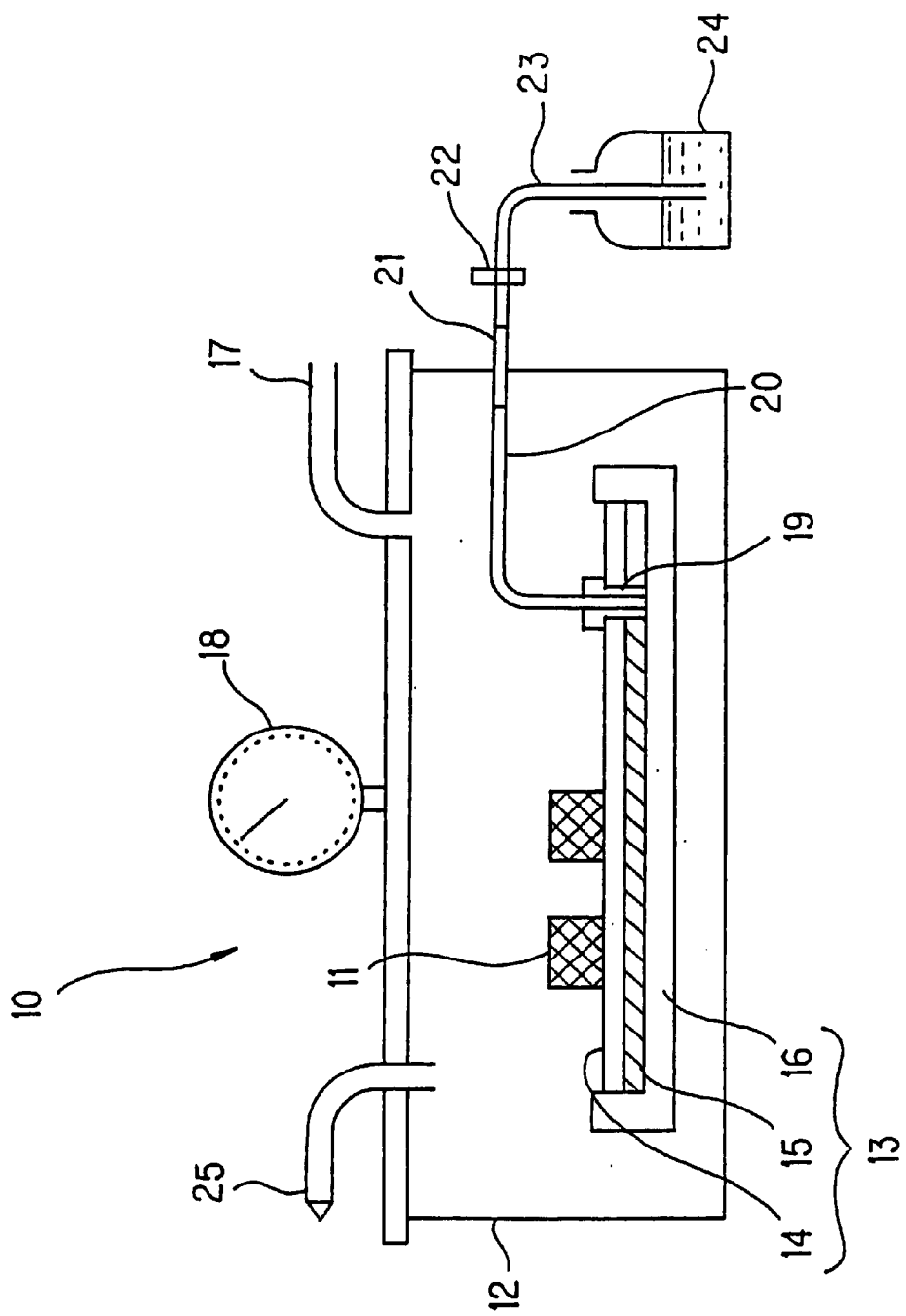
FIG. 3 is an illustration showing diagrammatically the pressure-plate method used to measure the correlation between pF value and volumetric water content (moisture retention curve)

First, the technology of the pressure-plate method is briefly described with reference to FIG. 3. A pressure-plate apparatus 10 consists of a pressure chamber 12 and a pressure plate 13. The pressure plate 13 consists of a porous ceramic plate 14 and a screen 15 fixed below which are covered with a rubber membrane 16. The pressure chamber 12 is equipped with a pressure gage 18 to read the air pressure inside the chamber.

A soil sample 11 is placed on top of the porous ceramic plate 14 saturated with water. When air pressure is applied from a pressure source through a communicating pipe 17, the soil water held at a potential greater than the matrix potential in equilibrium with the applied air pressure is depleted through the holes in the porous ceramic plate 14. The soil water passes through a metal drain hole 19, a pressure-resistant tube 20 and a drain port 21 in that order and then through a drain tube 23 having a pinch cock 22 to flow into a drain bin 24. An evacuation valve 25 is provided in the interest of evacuating the pressure chamber 12. By changing the air pressure stepwise, one can measure the water retentivity corresponding to a respective value of matrix potential. For each magnitude of the air pressure applied, the soil sample is taken out as it is placed on the pressure plate and its weight is measured. The moisture content of the soil sample is determined by calculating the difference between the weight of the measured soil sample and that of the same soil sample in a dry state. The determined moisture content corresponds to the applied air pressure, hence, the moisture potential at the time of measurement, thus providing a moisture content corresponding to a given pF value. One can also determine the volumetric soil water content on the basis of its bulk specific gravity.

This procedure is repeated with the air pressure being varied stepwise; as a result, a comparison table is constructed to provide a cross-reference between various pF values and the corresponding volume fractions of water. A moisture retention curve can be constructed in a graphical form from the values in the table by plotting the pF values on the horizontal axis and the volume fractions of water on the vertical axis.

The principle of the sand-column method which is a similar method for measuring the pF values of the soil is described below with reference to FIG. 4.

Figure 4:
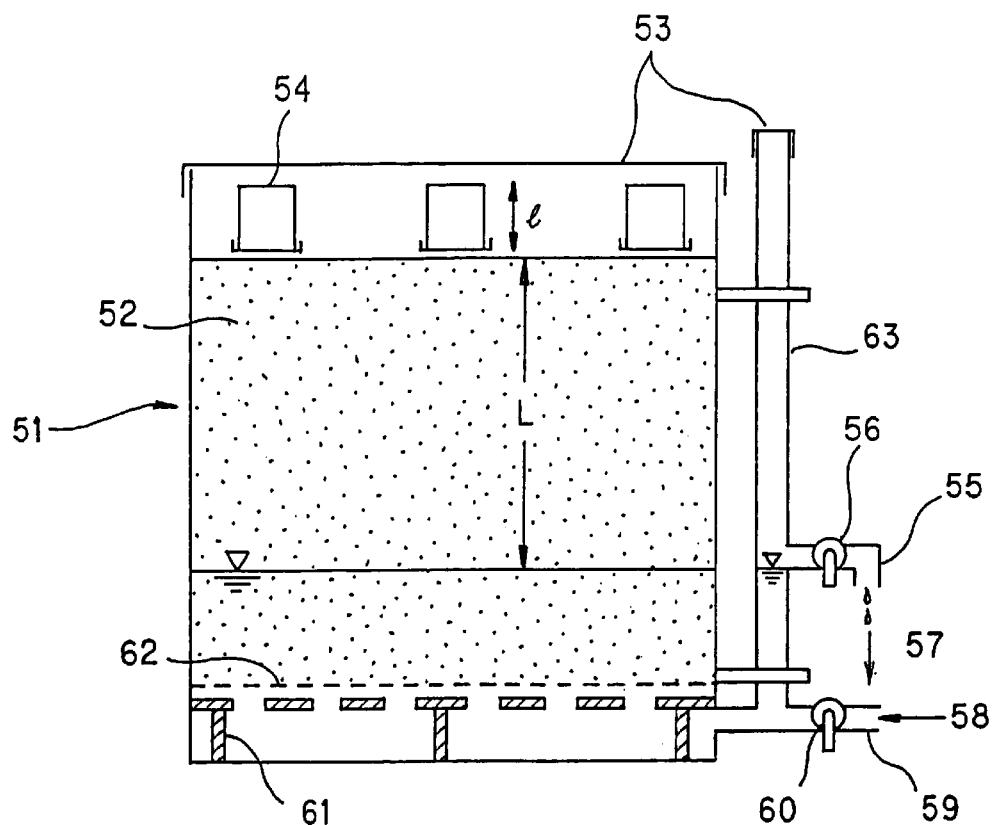
FIG. 4 is an illustration showing diagrammatically the sand-column method used to measure a moisture retention curve.

FIG. 4 is a diagrammatic representation of a sand-column apparatus generally indicated by 51. Usually, sand grains that have passed through a sieve finer than 250 μm or quartz sand grains adjusted to have sizes between 300 and 180 μm are employed. Sand grains 52 preliminarily washed with water are packed into a column and a cock 60 is opened so that tap water 58 is flowed in at an inlet port 59 to saturate the sand grains. A support platform 61 and a brass screen 62 are fixed in the bottom of the column to retain the sand column. The sand column is vibrated by, for example, tapping on the sidewall so as to stabilize the arrangement of sand grains. In order to prevent evaporation from its top, the sand column is covered with a polyethylene sheet or lid 53. It will be more effective if a soil sampling cylinder 54 is covered with such a lid. A soil sample (soil sampling cylinder) 54 is placed on the sand column 52, the height of a movable water outlet 55 is fixed to the top end of the sand column and the soil sample 54 is saturated with water. Then, the movable water outlet 55 is lowered to a specified position and a cock 56 is opened to drain excess water 57, whereby the level of the free water in the sand column is lowered to initiate dehydration of the soil sample. The water level L is read by a level meter 63. Upon completion of dehydration, the mass of the soil sample is measured to determine the volumetric water content of it. The matrix potential (cm) of the soil sample at that point in time is expressed as −(L+l/2) where l is the thickness of the soil sample. By this procedure, the volumetric water content of the soil sample at a given pF value can be measured.

This procedure is repeated with the water level L being varied stepwise to construct a comparison table which provides a cross-reference between various pF values and the corresponding volume fractions of water. A moisture retention curve can be constructed in a graphical form from the values in the table by plotting the pF values on the horizontal axis and the volume fractions of water on the vertical axis.

In a separate step, samples of the same soil with known volume fractions of water are subjected to measurement with, for example, an ADR instrument and its output signal values, for example, output voltages are measured to construct a calibrated table for converting the output voltage to the volumetric soil water content. By plotting the data in a graphical form, the output voltage on the horizontal axis and the volumetric water content on the vertical axis, one obtains a characteristic line of the shape shown in FIG. 2.

After thusly constructing the characteristic line, one measures the moisture content of the soil on site (in an ordinary field) using, for example, an ADR instrument. In the first step, the volumetric soil water content is determined from the output voltage of the ADR instrument on the basis of the preliminarily constructed line characteristic line describing the correlation between the output voltage and the volumetric water content. In the second step, the pF value of the oil can be determined from the determined volumetric soil water content on the basis of the preliminarily constructed moisture retention curve (the characteristic line describing the correlation between the volumetric water content and the pF value).

If the above-described two characteristic lines are loaded into a processor, the pF value of the soil can be calculated from the output voltage signal from the ADR instrument by means of an electronic circuit and the result is numerically presented on a display, thus realizing an extremely convenient measuring operation.

If desired, the signal for the calculated pF value of the soil may be sent to a control circuit associated with an irrigation apparatus in order to activate a water supply device in the irrigation apparatus.

Compared to the conventional approach using a tensiometer, the method of the invention enables the pF value of the soil to be measured directly and continuously in a by far convenient manner and the result of the measurement can be effectively used to control irrigation. In tensiometry, mediums made of coarse particles having porous surfaces as exemplified by pumice particles have defied the measurement of pF values; according to the method of the invention, pF values can be determined if the volumetric soil water content is measured by ADR and other methods that are also applicable to porous mediums.

Note that the pressure-plate method, the sand-column method and various other methods that are used in the present invention to measure the correlation between the pF value and the volumetric water content (i.e., moisture retention curve) are incapable of measurement on special soil and mediums, in particular, the soil (mediums) made of particles having porous surfaces. The reasons are as follows: if pumice particles with sizes of 1–5.6 mm are used as a medium, pressure application in the pressure-plate method does not guarantee the measurement of correct pF values since the water contained in the pumice particles does not form a continuous phase. In other words, the water contained in mediums such as the one made of pumice particles does not exist as a continuous phase and the resulting failure of capillary water to form continuous channels makes it impossible to measure the correct pF values. In the sand-column method, the water in the pumice medium does not form any liquid junction and there is no way to measure the correct pF values. Therefore, some special measures are necessary if soil composed of particles having porous surfaces is to be measured for pF values by the method of the present invention. This point will be discussed below in detail.

The present inventors studied the feasibility of measuring the pF values of a pumice medium by the pressure-plate method or the sand-column method. As a result, it was found that the correct measurement of pF values was impossible with a medium sample solely composed of coarse particles whereas the intended measurement was possible with a mixture of two mediums, one composed of coarse particles and the other made of fine particles. The present inventors prepared three soil samples, one being a medium composed of coarse particles, the second being a fine particulate sample prepared by pulverizing the first sample, and the third being a mixed soil sample which was a dispersion of the first and second samples in admixture; the inventors measured the pF values of the second and third samples and found that the pF values of the first soil sample could be determined by subjecting the results of the measurements to the "subtraction operation" described below. This process is described below in detail.

First, a coarse medium, for example, a medium consisting of coarse pumice particles with sizes of 1–5.6 mm is provided. Then, this coarse particulate medium is pulverized to form a fine particulate medium. The coarse particulate medium and the fine particulate medium are mixed and dispersed to make a mixed soil sample. In this case, the two mediums are preferably mixed in equal weights but this is not the absolute requirement as long as the mixing weight ratio is double-checked.

For the thus prepared fine particulate medium and the mixed soil sample, the relationship between the pF value and the volumetric water content (i.e., moisture retention curve) is determined by the pressure-plate method or the like. The applicable procedure is described below. In the following description, for the sake of convenience, the medium solely composed of coarse pumice particles will be called sample B, the fine particulate medium prepared from the coarse pumice particles will be called sample A, and the mixed soil sample prepared by mixing sample A with sample B will be called sample C, and the measurement of pF values by the pressure-plate method is given as an example.

Sample A composed of the fine particulate medium can be measured for pF values by the pressure-plate method but sample B of coarse pumice particles cannot be measured for pF values by the pressure-plate method. Nevertheless, the mixed soil sample C can be measured for pF values. This is probably because the fine particles get into the gaps between the coarse particles to prevent blow-through. Therefore, the particle size of the fine particulate medium sample which is to be used to prepare the mixed soil sample is desirably such that the fine particles can get into the gaps between the coarse particles. Further, the fine particles should not be small enough to get into pores in the porous coarse particles. If the fine particles got into pores in the porous coarse particles, a behavioral change would occur to make it impossible to obtain the correct pF values. Generally, the particle size of the fine particulate sample is preferably, but not limited to, within the range of from about 50 to about 200 $\mu$m.

As just mentioned above, pF values cannot be measured with the coarse particulate sample B but they can be measured with the fine particulate sample A and the mixed soil sample C. Hence, from the results of measurements with the mixed soil sample C and the fine particulate sample A, the result of measurement with sample B is determined by the "subtraction operation" described below.

For the mixed soil sample C and the fine particulate sample A, the relationship between the pF value and the volumetric water content, namely, the moisture retention curve, is measured by the pressure-plate method. The measurement is repeated with the wetness of each sample being varied in several ways.

If the volumetric water content of the mixed soil sample C at a given pF value is written as $x_c$ (v/v %) and if a given volume of the mixed soil sample has a moisture content of c (g), then the amount of water [$c_a$ (g)] held by the fine particles in the mixed soil sample is calculated by multiplying the moisture content [a (g)] of the same volume of fine particulate medium sample A at the stated pF value by the weight proportion of the fine particles in the mixed soil sample. In other words, $c_a = a \times (z_{ca}/z_a)$ where $z_{ca}$ (g) is the weight of the fine particles in the given volume of the mixed soil sample and $z_a$ (g) is the weight of the same volume of the fine particulate medium sample. Then, the amount of water [$c_a$ (g)] held by the fine particles in the mixed soil sample C is subtracted from the moisture content [c (g)] of the mixed soil sample C to give the amount of water [$c_b$ (g)] held by the coarse particles in the mixed soil sample C; in other words, $c_b = c - c_a$. The moisture content of the coarse particulate medium sample B can be calculated by dividing $c_b$ by the proportion of the coarse particulate medium in the mixed soil sample; in other words, $b = c_b \times (z_b/z_{cb})$ where $z_b$ (g) is the weight of the same volume of the coarse medium sample B and b (g) is the moisture content of the coarse particulate medium B. The volumetric water content (v/v %) of the coarse particulate medium sample B can be determined from the calculated moisture content b (g) of the coarse particulate medium sample.

In these measurements, the amounts of all samples are expressed in terms of weight. The coarse particles in the mixed soil sample have the surface water potential decreased if they are surrounded by the fine particles. However, owing to the porous nature of the coarse particles, this decrease in water potential is negligibly small since the surface area of the coarse particles that are surrounded by the fine particles is very small compared to the total surface area of the coarse particles (less than a hundredth of the latter).

The thus determined volumetric water content of the coarse particulate medium sample may safely be considered to correspond to the pF value of the sample. By repeating the above-described procedures of measurement and calculation, one can construct the moisture retention curve which describes the correlation between the volumetric water content of the coarse particulate medium and its pF value.

Similarly, the sand-column method is not capable of measuring the correct pF values of the coarse particulate sample since the water in the sample forms only interrupted liquid junctions. As it turned out, however, the fine particulate sample prepared by pulverizing the coarse particles as well as the mixed soil sample prepared by mixing the coarse particulate sample with this fine particulate sample can be correctly measured for pF values by the sand-column method. This is probably because the fine particles getting into the gaps between coarse particles help water form continuous liquid junctions. Hence, the sand-column method, if it is modified by the above-described procedure, can be applied to a soil sample made of coarse particles such as pumice particles and yet it produces a moisture retention curve describing the relationship between the pF value and the volumetric water content of the soil sample.

Using the thus constructed moisture retention curve as well as the calibrated correlation between the output voltage from an ADR instrument and the volumetric water content, one may perform ADR measurement on the soil and determine its pF value on the basis of its volumetric water content.

In summary, the method of the invention for measuring the pF value of the soil is implemented in different ways depending upon the nature of the soil.

For an ordinary type of soil, the following procedure is taken to measure its pF value:

(1) apply the pressure-plate method, the sand-column method or other suitable method to the soil under analysis and determine a moisture retention curve describing the relationship between the pF value of the soil and its volumetric water content;

(2) apply ADR or some other method to the soil to measure its dielectric constant by impressing electric pulses and on the basis of the relationship between the output signal value in the soil (output voltage in the case of ADR) and its volumetric water content, determine the volumetric soil water content of interest; the relationship (in calibrated values) between the output signal value and the volumetric soil water content under analysis should be determined prior to measurement;

(3) determine the pF value of the soil from the volumetric soil water content measured in step (2) on the basis of the moisture retention curve constructed in step (1).

For a soil sample made of porous coarse particles such as pumice particles, the following procedure is taken to measure its pF value:

(1) pulverize the sample of coarse particulate soil under analysis-to form a fine particulate sample; mix the coarse particulate soil sample with the fine particulate sample to form a mixed soil sample; provide equal volumes of the coarse particulate soil sample, the fine particulate sample and the mixed soil sample and measure their respective weights; apply the pressure-plate method, the sand-column method or other suitable method to the fine particulate sample and the mixed soil sample and determine a moisture retention curve for each sample which describes the relationship between the pF value of the soil and its volumetric water content; then apply the already described "subtraction operation" to the obtained results to determine a moisture retention curve for the coarse particulate soil;

(2) apply ADR or some other method to the soil to measure its dielectric constant by impressing electric pulses and on the basis of the relationship between the output signal value in the soil of interest (output voltage in the case of ADR) and the volumetric water content, determine the volumetric soil water content; the relationship (in calibrated values) between the output signal value and the volumetric soil water content under analysis should be determined prior to measurement;

(3) determine the pF value of the soil from the volumetric soil water content measured in step (2) on the basis of the moisture retention curve constructed in step (1).

In accordance with the invention, the pF value of the soil is determined by the above-described method of measuring its moisture content and irrigation of the soil is controlled on the basis of the determined pF value to realize cultivation of crops under optimum conditions. Specifically, the pF value of the soil is measured at given time intervals, each of the measured pF values is compared with the desired pF value, and the supply of irrigating water or the nutrient solution is controlled such that the pF value of the soil will not go outside the range of 1.7–2.7 which is optimal for crop cultivation. To this end, the desired pF value may be set at 2.0 and if the measured pF value is higher than this value, irrigating water or the nutrient solution is supplied but if the measured pF value is lower than the desired value, the supply of irrigating water or the nutrient solution is stopped.

The present invention also provides an apparatus for controlling irrigation in the manner described above. Thus, according to the other aspect of the invention, there is provided an apparatus for cultivation with a nutrient solution comprising a continuous drip applicator of a nutrient, means equipped with a nutrient flow valve for controlling the supply of the nutrient from the drip applicator, an instrument for measuring the volumetric water content of a medium, a processor which is loaded with a predetermined correlation between pF value and volumetric water content of the medium, which performs arithmetic operations for conversion to pF value from the volumetric water content of the medium as measured with the instrument for measuring the volumetric water content and which outputs a signal for the pF value of the medium on the basis of the result as outputted from the instrument for measuring the volumetric water content, and means for controlling the drip applicator by controlling the supply of the nutrient to the drip applicator on the basis of a signal for pF value as outputted from said processor. According to another preferred aspect of the invention, there is provided an apparatus for cultivation with a nutrient solution comprising a continuous drip applicator of a nutrient, means equipped with a nutrient flow valve for controlling the supply of the nutrient from the drip applicator, an ADR instrument having a probe to be inserted into a medium, a processor which is loaded with two predetermined correlations for the medium, one being between pF value and volumetric water content and the other being between the output voltage from the ADR instrument and the volumetric water content, which performs arithmetic operations for conversion from the output voltage of the ADR instrument to the volumetric water content of the medium and for conversion to pF value from the volumetric water content of the medium and which outputs a signal for the pF value of the medium on the basis of the output voltage of the ADR instrument, and means for controlling the drip applicator by controlling the supply of the nutrient to the drip applicator on the basis of a signal for pF value as outputted from said processor.

The above-described method for controlling irrigation may be implemented by an apparatus for cultivation with a nutrient solution on a solid medium which comprises a continuous drip applicator of a nutrient, an ADR instrument having a probe to be inserted into a medium and control means for controlling the supply of the nutrient to the drip applicator in response to the output voltage from said ADR instrument and which is timer-controlled to operate in response to the output voltage from the ADR instrument at given time intervals. In order to control the supply of the nutrient to the drip applicator in response to the output voltage from the ADR instrument, the means for controlling the drip applicator is preferably designed as follows: the processor is loaded with two predetermined correlations for the medium of interest, one being between pF value and volumetric water content and the other being between the output voltage from the ADR instrument and the volumetric water content, and the processor performs arithmetic operations for conversion from the output voltage of the ADR instrument to the volumetric water content of the medium and for conversion to pF value from the volumetric water content of the medium and outputs a signal for the pF value of the medium on the basis of the output voltage of the ADR instrument, and the supply of the nutrient to the drip applicator is controlled on the basis of the signal for pF value outputted from said processor. The period at which the degree of opening of the nutrient flow valve is adjusted on the basis of a measured pF value depends on the required strictness in control, which in turn depends on the kind of crop to be cultivated; generally speaking, the supply of irrigating solution or the nutrient is controlled at an interval of 10 minutes to 2 hours, preferably at an interval of 10–20 minutes, on the basis of the measured pF value.

In the above description, the volumetric water content is measured by ADR; however, as already mentioned, the TDR instrument, the FDR instrument and other types of instrument may also be used as long as they can measure the volumetric water content on the basis of the dielectric constant. It should also be noted that the dielectric constant based technique is not the sole method that can be used to measure the volumetric soil water content and any methods can be used in the invention as long as they are capable of direct measurement of the volumetric soil water content in a field.

The soil whose pF value can be measured by the method of the invention may be exemplified by not only the so-called "soil" described above but also porous mediums including pumice and charcoal. As for the medium made of pumice, precise measurement can be accomplished even if it is made of SHIRASU pumice.

The definition of SHIRASU pumice as well as its description may be found in "Tsuchi no Kankyoken", supra, pp. 30–32. According to the definition, SHIRASU pumice is the generic name for "non-fused portions of the deposits of pyroclastic pumice flows ejected from large caldera volcanos in the late Pleistocene, or secondary deposits of such portions". In Japan, the SHIRASU from the southern part of Kyushu is famous. SHIRASU of the same nature is also distributed around Lake Kussharo, Lake Shikotsu, Lake Toya and Lake Towada, as well as around caldera volcanos such as Mt. okachidake and Mt. Aso. In surface layer geological maps such as those prepared by the National Land Agency in a basic survey of land classifications, SHIRASU is shown as the deposits of pumice flows.

Examples of the crops that can be cultivated by the method of the invention with nutrient solutions include the following: vegetable fruits such as tomato, cherry tomato, cucumber, eggplant, pimento, paprika, (jumbo green pepper), okra, kidney bean, garden pea, bitter gourd, luffa, watermelon and melon; leaf vegetables such as corn salad, spinach, Brassica Rapa var. pervidis, Japanese ginger, mulukhiya, Water convolvulus, Qing gin cai, leaf lettuce, Coriander, aloe, *Cryptotaenia japonica*, Welsh onion, celery, parsley, crown daisy and raddish; fruits such as pineapple, passion fruit, papaya and strawberry; flowers such as carnation, chrysanthemum, rose, cactus, trumpet lily, Russell prairie gentian, curcuma, orchid and pansy.

EXAMPLES

The following examples are provided to further illustrate the invention but are in no way to be taken as limiting the scope of the invention.

Example 1 Measuring the Volumetric Water Content by ADR

A sample of SHIRASU pumice (product of Kagoshima Prefecture, Kyushu, Japan) having particle sizes in the range of 1–5.6 mm was assayed by ADR with its wetness being varied to investigate the relationship between the output voltage of the ADR instrument and the volumetric water content of the pumice medium. The output voltage of the ADR instrument was plotted in a graphical form on the horizontal axis and the volumetric water content on the vertical axis to construct a curve of the shape shown in FIG. 2.

Example 2 Calculating the pF Value from the Volumetric Water Content

1. Preparing Samples

Two soil samples were provided, one being a sample of SHIRASU pumice (product of Kagoshima Prefecture, Kyushu, Japan) having particle sizes in the range of 1–5.6 mm and the other being a fine particulate pumice sample that was prepared by pulverizing the SHIRASU pumice to particle sizes in the range of about 50–200 μm. The two samples, each measuring 100 ml, had different weights; the pumice sample weighed 53 g and the fine particulate pumice sample 79.4 g. The two samples were mixed in nearly equal weights to prepare a mixed soil sample. A hundred milliliters of the mixed soil sample weighed 72.5 g and it consisted of 35.2 g of the pumice sample and 37.3 g of the fine particulate pumice sample.

2. Measuring the pF Value and the Volumetric Water Content

The mixed soil sample was measured for the volumetric water content at various pF values by the pressure-plate method. Similarly, the fine particulate pumice sample was measured for the volumetric water content at various pF values by the pressure-plate method. The two measurements were repeated with the wetness of the samples varied in several ways. The pressure-plate method was used to measure pF values because the range of pF values that could be measured by the pressure-plate method were in good agreement with the range of pF values held as a suitable condition for the actual cultivation.

3. Calculating the Moisture Content of the Pumice Component in the Mixed Soil Sample As is clear from Table 1 which shows the results of the measurements, the mixed sample M had a pF value of 1.6 when its volumetric water content was 44.8 (v/v %). At the same pF value, the fine particulate pumice sample P had a volumetric water content of 53.3 (v/v %).

By subtracting the moisture content (g) of the fine particulate pumice component in the mixed sample M from the moisture content (g) of the mixed sample, one can determine the moisture content of the pumice component in the mixed sample, from which one can calculate the volumetric water content of the pumice sample.

The moisture content [A3] in 100 ml of the mixed sample M is found to be 44.8 g from its volumetric water content [A2]. The moisture content [A4] of the fine particulate pumice component (37.3 g) in 100 ml of the mixed sample is calculated as [53.3×(37.3/79.4)]=25.1 g.

Then, the moisture content [A5] of the pumice component in the mixed sample M is ([A3]−[A4])=(44.8−25.1)=19.7 g.

Since this is the moisture content in 35.2 g of the pumice sample, it must be converted to a value for the case where its volume (100 ml) is entirely filled with the pumice (whose weight is 53 g); the result is [19.7×(53/35.2)]=29.7 g.

This moisture content is what is found in 100 ml of the pumice sample, it then follows that the volumetric water content of the pumice sample is 29.7 (v/v %). One may therefore conclude that the pumice sample under consideration has a volumetric water content of 29.7 (v/v %) at a pF of 1.6.

The same procedure was repeated at several pF values to determine the correlation between the pF value and the volumetric water content. The results are shown in Table 1 for the two soil samples at pF values of 1.6, 1.8, 2, 2.2, 2.5 and 2.7. The same measurements were made over the pF range of 0.4–2.8 and the results are shown graphically in FIGS. 5a and 5b for the fine particulate pumice sample and the mixed soil sample, respectively. A moisture retention curve for the pumice sample was calculated from these results and shown in FIG. 5c.

Looking at the relationship between the pF value of the pumice sample and its volumetric water content that is shown graphically in FIG. 5c, one can see the following: the method of Example 2 is not fully applicable within the pF range of 1.6–2.0 since the curve is substantially flat; on the other hand, a certain correlation was found to exist between the pF value and the volumetric water content in the pF range of 2.0–2.7 and could be effectively used as an index for controlling the irrigation of mediums.

Using the moisture retention curve obtained in Example 2, one can easily convert the values of ADR based volumetric water content in Example 2 to the pF values of the medium that needs to be controlled for irrigation.

TABLE 1

| Description | pF value | | | | | |
|---|---|---|---|---|---|---|
| | 1.6 | 1.8 | 2 | 2.2 | 2.5 | 2.7 |
| A1 Volumetric water content of the fine particulate pumice sample (v/v %) | 53.3 | 50.0 | 46.3 | 42.6 | 38 | 33.5 |
| A2 Volumetric water content of the mixed soil sample (v/v %) | 44.8 | 43 | 41.5 | 38.3 | 33.7 | 29.8 |
| A3 Moisture content of the mixed soil sample (g) | 44.8 | 43 | 41.5 | 38.3 | 33.7 | 29.8 |
| A4 Amount of water held by fine particles in the mixed sample (g) | 25.1 | 23.5 | 21.8 | 20.0 | 17.9 | 15.7 |
| A5 Amount of water held by pumice in the mixed sample (g) | 19.7 | 19.5 | 19.7 | 18.3 | 15.8 | 14.1 |
| A6 Volumetric water content of pumice sample (v/v %) | 29.7 | 29.4 | 29.7 | 27.6 | 23.8 | 21.2 |
| ADR output signal (mV) | 268 | 266 | 268 | 254 | 229 | 212 |

Example 3 Controlling Irrigation by ADR

Figure 6:
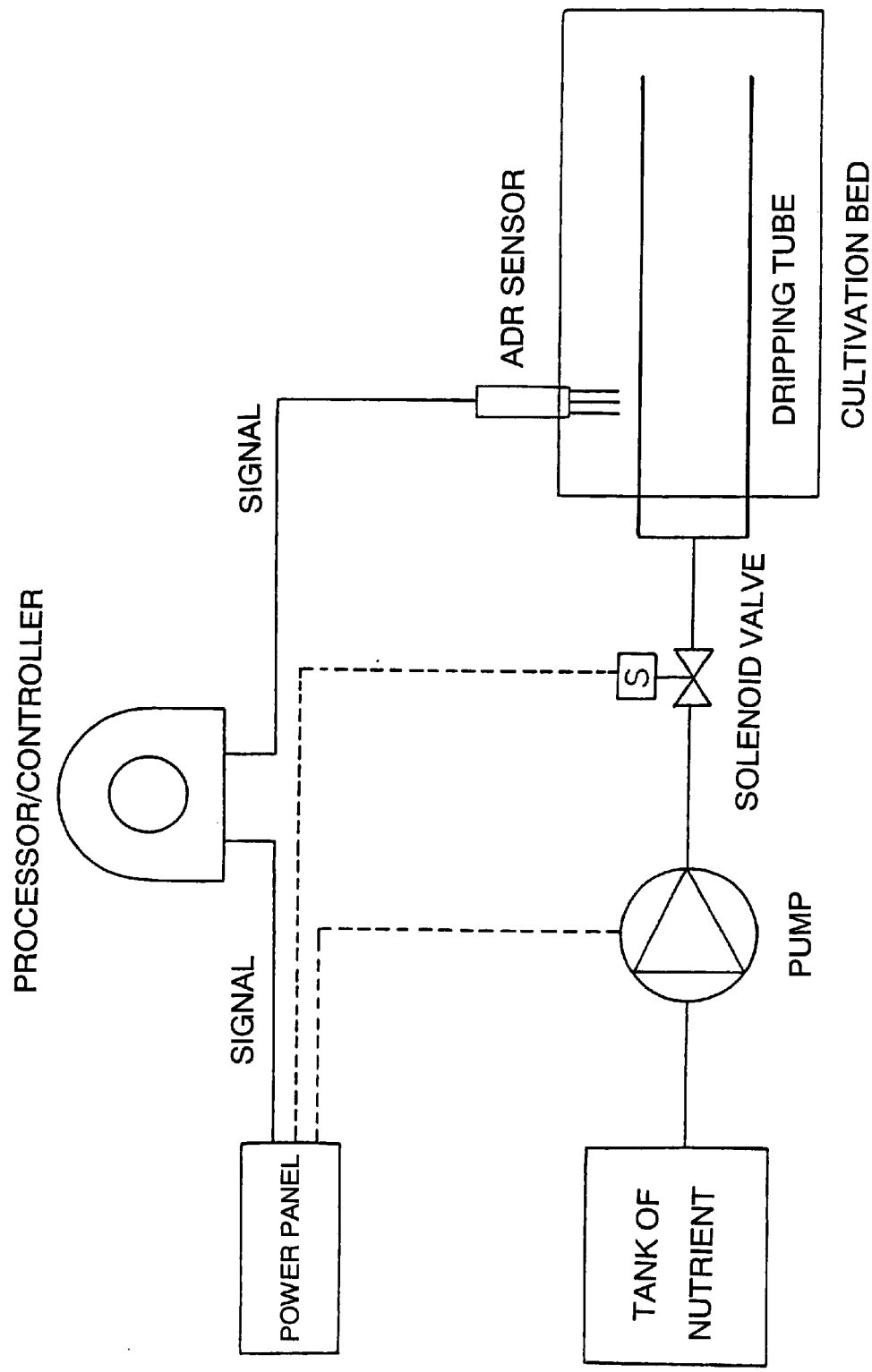
FIG. 6 is a diagram showing an outline of the culture apparatus capable of automated irrigation control which was used in Example 3 of the invention.

Corn salad was cultivated on a medium of SHIRASU pumice (product of Kagoshima Prefecture, Kyushu, Japan) having particle sizes in the range of 1–5.6 mm. The nutrient was of a standard recipe recommended by a horticultural experiment station [abbreviated as ES recipe, the nutrient had the following composition: N=16 (meq/L as applicable hereunder); P=4; K=8; Ca=8; Mg=4]. A plurality of cell trays were provided and one seed of corn salad was sown on each tray. After 21 days of nursing, the seedlings were transplanted to a leaf vegetable cultivation bed for setting at a density of 42 plants per square meter. The planted area was 4 $m^2$. For both nursing of the seedlings and their cultivation after transplantation, automated irrigation was performed using the system shown in FIG. 6. Briefly, the dielectric constant of the medium was measured with an ADR sensor and converted to a corresponding pF value by means of a processor/controller loaded with the correlations obtained in Examples 1 and 2; irrigation was controlled on the basis of the thus obtained pF values. Specifically, the desired pF was set at 2.0; when the measured pF value exceeded this value, the processor/controller automatically operated the power panel to activate the pump and the solenoid valve, thereby starting irrigation; when the measured pF value dropped to 2.0, irrigation was stopped. Thirty-five days after transplantation, the crops were harvested to give a yield of 3203 g/$m^2$. During the period from transplantation to harvesting, the nutrient was used in a volume of 84.6 L/$m^2$.

Comparative Example 1 Timer Controlled Irrigation

In parallel with the experiment being conducted in Example 3, corn salad was cultivated by repeating the procedure of Example 3 except that irrigation was timer controlled to take place twice a day, at 9 o'clock in the morning and 3 o'clock in the afternoon, and continued until excess nutrient came out of the cultivation bed. The yield was 2694 g/$m^2$. During the period from transplantation to harvesting, the nutrient was used in a volume of 148.6 L/$m^2$. As the cultivation approached the harvest time, a mold-like growth became visible on the surface of the cultivation bed, indicating that the nutrient had been supplied in an amount more than necessary for the actual growth of corn salad.

Comparing Example 3 with Comparative Example 1, one can see that the cultivation using the invention method of irrigation control could achieve a higher yield using a smaller amount of nutrient than when the conventional timer-controlled method of irrigation was adopted. Thus, according to the method of the invention, the amount of a nutrient can be controlled precisely such that it is supplied in the quantity actually required by the crop being cultivated and this helps prevent the nutrient from being supplied in excess amount that is simply wasted as liquid emissions and the like.

Industrial Applicability

According to the present invention, the pF value of the soil can be measured by a simple method without using the conventional tensiometer. Since this measurement can be achieved by ADR and other convenient methods, a simple and convenient apparatus will suffice and reproducible data are obtained to permit simple measurements in ordinary fields. In the case of solid mediums made of pumice and other coarse particulate matter, the conventional methods such as the pressure-plate method have been incapable of correctly measuring the moisture retention curve which describes the correlation between the pF value and the volumetric water content. This is not the case in the preferred aspect of the invention and even with a coarse particulate soil sample, the correct moisture retention curve can be determined by the pressure-plate method and the like and the pF value of such soil can be measured in a simple way. Hence, regardless of soil texture, soil management can be easily performed to prevent drying of the soil or realize irrigation.

The invention also enables the supply of nutrients to be controlled on the basis of pF value in cultivation on solid mediums and the nutrient can be supplied in amounts that keep pace with the growth of the crop being cultivated, contributing to a higher yield of the crop. Since the pF value can be controlled automatically, the intended control is easy to achieve requiring no manpower, thus contributing to labor saving.

Saving energy, resources and labor, the present invention is very effective for the purpose of preserving environmental resources. The water required for cultivation can be reduced to a minimum amount whereas the fertilizer can be utilized to the fullest extent; hence, only a small amount of fertilizer will be discharged unabsorbed, reducing the likelihood of eutrophication of water bodies and profuse growth of algae due to wastewater. Continuous drip irrigation on the rock wool medium is extensively practiced today in crop cultivation but the spent rock wool medium has been found to cause an extremely serious problem as an industrial waste. Another crucial problem is the liquid emission due to excessive supply of the nutrient. Using the pumice medium and adopting the invention method for irrigation control, one can solve the two problems simultaneously and this is indeed a great benefit from the viewpoint of protecting both resources and the environment.

What is claimed is:

1. A method for measuring the pF value (soil moisture tension) of a coarse particle medium composed of coarse particles having porous surfaces and a particle size of 1–5.6 mm, comprising the steps of:
   (a) preliminarily determining a predetermined correlation between pF value and volumetric water content of the coarse particle medium to be measured, by
      (i) pulverizing a sample of the coarse particle medium to prepare a fine particulate sample,
      (ii) mixing a sample of the coarse particles with the fine particulate sample in a predetermined weight ratio to prepare a mixed particulate sample,
      (iii) determining a correlation between volumetric water content and the pf value for the mixed particulate sample and for the fine particulate sample, and
      (iv) determining the predetermined correlation between volumetric water content and the pf value for the coarse particle medium on the basis of the correlations between volumetric water content and the pf value obtained for the mixed particulate sample and for the fine particulate sample,
   (b) measuring the volumetric water content of the coarse particle medium; and
   (c) converting the value of the volumetric water content of the coarse particle medium measured in the above step (b) to the pf value of the coarse particle medium on the basis of the predetermined correlation between pF value and volumetric water content preliminarily determined in the above step (a).

2. The method according to claim 1, wherein the volumetric water content of the coarse particle medium is measured by amplitude-domain reflectometry (ADR) method, time-domain reflectometry (TDR) method or frequency-domain reflectometry (FDR) method.

3. The method according to claim 2, wherein the correlation between the output signal value of a sensor selected from among an ADR instrument, a TDR instrument or an FDR instrument and the volumetric water content of the coarse particle medium is preliminarily determined for the coarse particle medium to be measured and the output signal value obtained with the sensor is converted to the volumetric water content of the coarse particle medium on the basis of the preliminarily determined predetermined correlation between the output signal value and the volumetric water content of the soil.

4. The method according to claim 3, wherein two predetermined correlations for the coarse particle medium to be measured, one being between pF value and volumetric water content and the other being between the output signal value of the sensor and the volumetric water content, are loaded into a processor and the conversion from the output signal value of the sensor to the volumetric water content of the coarse particle medium and the conversion to pF value from the volumetric water content of the coarse particle medium are performed with the processor by arithmetic operations.

5. The method according to claim 1, wherein the coarse particle medium is pumice.

6. The method according to claim 5, wherein the volumetric water content of the coarse particle medium is measured by amplitude-domain reflectometry (ADR) method, time-domain reflectometry (TDR) method or frequency-domain reflectometry (FDR) method.

7. The method according to claim 6, wherein the correlation between the output signal value of a sensor selected from among an ADR instrument, a TDR instrument or an FDR instrument and the volumetric water content of the coarse particle medium is preliminarily determined for the coarse particle medium to be measured and the output signal value obtained with the sensor is converted to the volumetric water content of the coarse particle medium on the basis of the preliminarily determined predetermined correlation between the output signal value and the volumetric water content of the soil.

8. The method according to claim 7, wherein two predetermined correlations for the coarse particle medium to be measured, one being between pF value and volumetric water content and the other being between the output signal value of the sensor and the volumetric water content, are loaded into a processor and the conversion from the output signal value of the sensor to the volumetric water content of the coarse particle medium and the conversion to pF value from the volumetric water content of the coarse particle medium are performed with the processor by arithmetic operations.

9. The method according to claim 5, wherein the correlations between the volumetric water content and the pF value for the mixed particulate sample and the fine particulate sample are determined by the pressure-plate method or the sand-column method.

10. A method for controlling coarse particle medium irrigation which, on the basis of the pF value of the coarse particle medium as measured by the method according to claim 5, controls the amount of supply of irrigating water or nutrient such that the coarse particle medium will have a pF value appropriate for crop cultivation.

11. The method for controlling coarse particle medium irrigation according to claim 12 which comprises measuring the pF value of the coarse particle medium at a timer-determined period and controlling the amount of supply of irrigating water or nutrient on the basis of the measured pF value of the coarse particle medium.

12. The method according to claim 1, wherein the correlations between the volumetric water content and the pF value for the mixed particulate sample and the fine particulate sample are determined by the pressure-plate method or the sand-column method.

13. A method for controlling coarse particle medium irrigation which, on the basis of the pF value of the coarse particle medium as measured by the method according to claim 1, controls the amount of supply of irrigating water or nutrient such that the coarse particle medium will have a pF value appropriate for crop cultivation.

14. The method for controlling coarse particle medium irrigation of the according to claim 13 which comprises measuring the pF value of the coarse particle medium at a timer-determined period and controlling the amount of supply of irrigating water or nutrient on the basis of the measured pF value of the coarse particle medium.

15. An apparatus for cultivation with a nutrient solution comprising:

a continuous drip applicator of a nutrient;

means equipped with a nutrient flow valve for controlling the supply of the nutrient from the drip applicator;

an instrument for measuring the volumetric water content of a medium;

a processor which is loaded with a predetermined correlation between pF value and volumetric water content of the medium, which performs arithmetic operations for conversion to pF value from the volumetric water content of the medium as measured with the instrument for measuring the volumetric water content and which outputs a signal for the pF value of the medium on the basis of the result as outputted from the instrument for measuring the volumetric water content; and means for controlling the drip applicator by controlling the supply of the nutrient to the drip applicator on the basis of a signal for pF value as outputted from said processor.

16. An apparatus for cultivation with a nutrient solution comprising:

a continuous drip applicator of a nutrient;

means equipped with a nutrient flow valve for controlling the supply of the nutrient from the drip applicator;

a sensor from among an amplitude-domain reflectometry (ADR) instrument, a time-domain reflectometry (TDR) instrument and an frequency-domain reflectometry (FDR) instrument each having a probe to be inserted into a medium;

a processor which is loaded with two predetermined correlations for the medium, one being between pF value and volumetric water content and the other being between the output signal value from the sensor and the volumetric water content, which performs arithmetic operations for conversion from the output signal value of the sensor to the volumetric water content of the medium and for conversion to pF value from the volumetric water content of the medium and which outputs a signal for the pF value of the medium on the basis of the output signal value of the sensor; and means for controlling the drip applicator by controlling the supply of the nutrient to the drip applicator on the basis of a signal for pF value as outputted from said processor.

* * * * *